(12) United States Patent
Pittenger et al.

(10) Patent No.: US 6,387,369 B1
(45) Date of Patent: *May 14, 2002

(54) CARDIAC MUSCLE REGENERATION USING MESENCHYMAL STEM CELLS

(75) Inventors: Mark F. Pittenger, Severna Park; Stephen L. Gordon, Columbia; Alastair Morgan Mackay, Towson, all of MD (US)

(73) Assignee: Osiris Therapeutics, Inc., Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,952

(22) PCT Filed: Jul. 14, 1998

(86) PCT No.: PCT/US98/14520

§ 371 Date: Mar. 27, 2000

§ 102(e) Date: Mar. 27, 2000

(87) PCT Pub. No.: WO99/03973

PCT Pub. Date: Jan. 28, 1999

Related U.S. Application Data

(60) Provisional application No. 60/052,910, filed on Jul. 14, 1997.

(51) Int. Cl.$^7$ .................. A61K 35/28; A61K 35/34; C12N 5/06; C12N 5/08

(52) U.S. Cl. ............... 424/93.7; 424/93.1; 424/93.2; 424/577; 424/569; 435/325; 435/366; 435/372; 435/375; 435/377

(58) Field of Search .................... 435/325, 366, 435/372, 440, 455, 377, 375; 424/93.1, 93.2, 93.7, 569, 577; 536/23.5, 23.51

(56) References Cited

U.S. PATENT DOCUMENTS

| 5,226,914 A | 7/1993 | Caplan et al. ............. 623/16 |
| 5,591,625 A | 1/1997 | Gerson et al. ........... 435/240.2 |
| 6,099,832 A | 8/2000 | Mickle et al. ........... 424/93.21 |

OTHER PUBLICATIONS

Prockop, D., Science, 276:71–74, 1997.*
Gerson, S., Nature Medicine, 5:262–264, 1999.*
Verma et al., Nature, 389:239–242, 1997.*
Orkin et al., in Report And Recommendations Of The Panel To Assess The NIH Investment In Research On Gene Therapy, Dec. 7, 1995.*
Robinson, et al., "Implantation of Skeletal Myoblast—Derived Cells", in *Cellular Cardiomyoplasty: Myocardial Repair with Cell Implantation*. Kao, et al., eds., Landes Bioscience, pp. 81–107 (1997).
Bruder, et al., *J. Cell. Biochem.*, vol. 56, pp. 283–294 (1994).
Warejcka, et al., *J. Surg. Res.*, vol. 62, pp. 233–242 (1996).
Krebsbach, et al., *Transplantation*, vol. 63, pp. 1059–1069 (Apr. 27, 1997).

* cited by examiner

*Primary Examiner*—Deborah J. R. Clark
*Assistant Examiner*—Janet M Kerr
(74) *Attorney, Agent, or Firm*—Elliot M. Olstein; Raymond J. Lillie

(57) ABSTRACT

Disclosed is a method for producing cardiomyocytes in vivo by administering to the heart of an individual a cardiomyocyte producing amount of mesenchymal stem cells. These cells can be administered as a liquid injectable or as a preparation of cells in a matrix which is or becomes solid or semi-solid. The cells can be genetically modified to enhance myocardial differentiation and integration. Also disclosed is a method for replacing cells ex vivo in a heart valve for implantation.

17 Claims, 2 Drawing Sheets

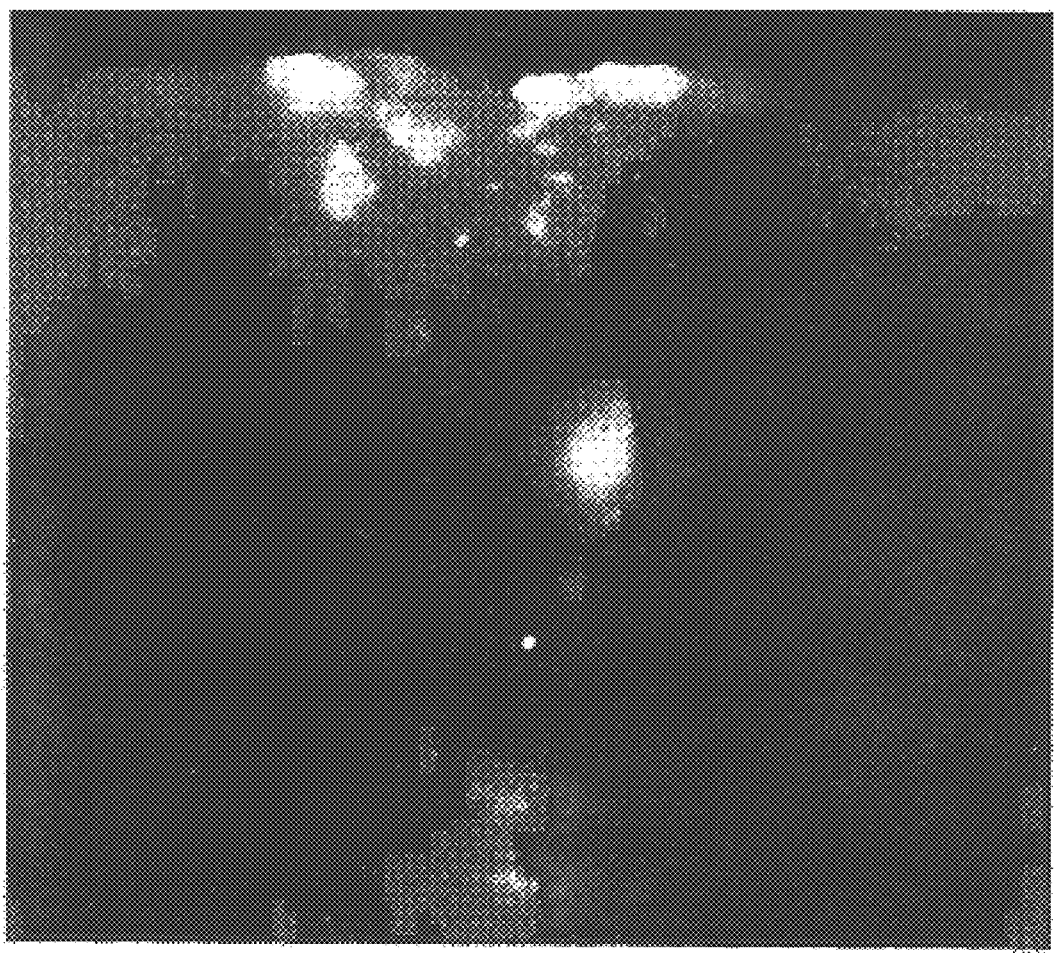
FIG. IC

CARDIAC MUSCLE REGENERATION USING MESENCHYMAL STEM CELLS

This application claims priority of U.S. provisional application Ser. No. 60/052,910, filed Jul. 14, 1997. This invention relates to the replacement and regeneration of cardiac tissue and muscle.

BACKGROUND OF THE INVENTION

This year over 300,000 Americans will die from congestive heart failure. The ability to augment weakened cardiac muscle would be a major advance in the treatment of cardiomyopathy and heart failure. Despite advances in the medical therapy of heart failure, the mortality due to this disorder remains high, where most patients die within one to five years after diagnosis.

A common heart ailment in the aging population is improper heart valve function, particularly the aortic valve. Mechanical replacement valves are widely used but require the patient to continually take blood thinners. Valves obtained from cadavers and xenographs (porcine) are also frequently used to replace a patient's own tissue. Valves are freeze-dried or chemically cross-linked using e.g., glutaraldehyde to stabilize the collagen fibrils and decrease antigenicity and proteolytic degradation. However, these valves remain acellular and often fail after several years due to mechanical strain or calcification. A replacement valve derived from biocompatible material that would allow ingrowth of the appropriate host cells and renewal of tissue over time would be preferred.

Mesenchymal stem cells (MSCs) are cells which are capable of differentiating into more than one type of mesenchymal cell lineage. Mesenchymal stem cells (MSCs) have been identified and cultured from avian and mammalian species including mouse, rat, rabbit, dog and human (See Caplan, 1991, Caplan et al. 1993 and U.S. Pat. No. 5,486,359). Isolation, purification and culture expansion of hMSCs is described in detail therein.

SUMMARY OF THE INVENTION

In accordance with the present invention mesenchymal stem cells (MSCs) are used to regenerate or repair striated cardiac muscle that has been damaged through disease or degeneration. The MSCs differentiate into cardiac muscle cells and integrate with the healthy tissue of the recipient to replace the function of the dead or damaged cells, thereby regenerating the cardiac muscle as a whole. Cardiac muscle does not normally have reparative potential. The MSCs are used, for example, in cardiac muscle regeneration for a number of principal indications: (i) ischemic heart implantations, (ii) therapy for congestive heart failure patients, (iii) prevention of further disease for patients undergoing coronary artery bypass graft, (iv) conductive tissue regeneration, (v) vessel smooth muscle regeneration and (vi) valve regeneration. Thus the MSCs are also used to integrate with tissue of a replacement heart valve to be placed into a recipient. The MSCs, preferably autologous, repopulate the valve tissue, enabling proper valve function.

MSC cardiac muscle therapy is based, for example, on the following sequence: harvest of MSC-containing tissue, isolation/expansion of MSCs, implantation into the damaged heart (with or without a stabilizing matrix and biochemical manipulation), and in situ formation of myocardium. This approach is different from traditional tissue engineering, in which the tissues are grown ex vivo and implanted in their final differentiated form. Biological, bioelectrical and/or biomechanical triggers from the host environment may be sufficient, or under certain circumstances, may be augmented as part of the therapeutic regimen to establish a fully integrated and functional tissue.

Accordingly, one aspect of the present invention provides a method for producing cardiomyocytes in an individual in need thereof which comprises administering to said individual a myocardium-producing amount of mesenchymal stem cells. The mesenchymal stem cells that are employed may be a homogeneous composition or may be a mixed cell population enriched in MSCs. Homogeneous human mesenchymal stem cell compositions are obtained by culturing adherent marrow or periosteal cells; the mesenchymal stem cells may be identified by specific cell surface markers which are identified with unique monoclonal antibodies. A method for obtaining a cell population enriched in mesenchymal stem cells is described, for example, in U.S. Pat. No. 5,486,359.

The administration of the cells can be directed to the heart, by a variety of procedures. Localized administration is preferred. The mesenchymal stem cells can be from a spectrum of sources including, in order of preference: autologous, allergenic or xenogeneic. There are several embodiments to this aspect, including the following.

In one embodiment of this aspect, the MSCs are administered as a cell suspension in a pharmaceutically acceptable liquid medium for injection. Injection, in this embodiment, can be local, i.e. directly into the damaged portion of the myocardium, or systemic. Here, again, localized administration is preferred.

In another embodiment of this aspect, the MSCs are administered in a biocompatible medium which is, or becomes in situ at the site of myocardial damage, a semi-solid or solid matrix. For example, the matrix may be (i) an injectible liquid which "sets up" (or polymerizes) to a semi-solid gel at the site of the damaged myocardium, such as collagen and its derivatives, polylactic acid or polyglycolic acid, or (ii) one or more layers of a flexible, solid matrix that is implanted in its final form, such as impregnated fibrous matrices. The matrix can be, for example, Gelfoam (Upjohn, Kalamazoo, Mich.). The matrix holds the MSCs in place at the site of injury, i.e. serves the function of "scaffolding". This, in turn, enhances the opportunity for the administered MSCs to proliferate, differentiate and eventually become fully developed cardiomyocytes. As a result of their localization in the myocardial environment they then integrate with the recipient's surrounding myocardium. These events likewise occur in the above liquid injectible embodiment, but this embodiment may be preferred where more rigorous therapy is indicated.

In another embodiment of this aspect, the MSCs are genetically modified or engineered to contain genes which express proteins of importance for the differentiation and/or maintenance of striated muscle cells. Examples include growth factors (TGF-β, IGF-1, FGF), myogenic factors (myoD, myogenin, Myf5, MRF), transcription factors (GATA-4), cytokines (cardiotrophin-1), members of the neuregulin family (neuregulin 1, 2 and 3) and homeobox genes (Csx, tinman, NKx family). Also contemplated are genes that code for factors that stimulate angiogenesis and revascularization (e.g. vascular endothelial growth factor (VEGF)). Any of the known methods for introducing DNA are suitable, however electroporation, retroviral vectors and adeno-associated virus (AAV) vectors are currently preferred.

Thus, in association with the embodiment of the above aspect using genetically engineered MSCs, this invention also provides novel genetically engineered mesenchymal stem cells and tissue compositions to treat the above indications. The compositions can include genetically modified MSCs and unmodified MSCs in various proportions to regulate the amount of expressed exogenous material in relationship to the total number of MSCs to be affected.

The invention also relates to the potential of MSCs to partially differentiate to the cardiomyocyte phenotype using in vitro methods. This technique can under certain circumstances optimize conversion of MSCs to the cardiac lineage by predisposing them thereto. This also has the potential to shorten the time required for complete differentiation once the cells have been administered.

BRIEF DESCRIPTION OF THE DRAWINGS

FIGS. 1A–1C show cardiac muscle injected, using a fine needle, with in vitro dye-labeled MSCs. The lipophilic dyes PKH26 (Sigma Chemical) or CM-Di I (Molecular Probes) were utilized to label MSCs prior to being introduced into animals. These dyes remain visible when the tissue site is harvested 1–2 months later. We have also shown that such dyes do not interfere with the differentiation of MSCs in in vitro assays. FIG. 1A shows the low magnification image of a rat heart which has been injected with dye labeled cells and later, a T-incision has been made at the site. FIGS. 1A and 1B reveal the labeled MSCs in the ventricle wall viewed from the outer surface. FIG. 1C shows a cross-section of the ventricle wall and that the cells are present in the outer 1–2 mm of the 3 mm thick cardiac muscle.

DETAILED DESCRIPTION OF PREFERRED EMBODIMENTS

Figure 1A:
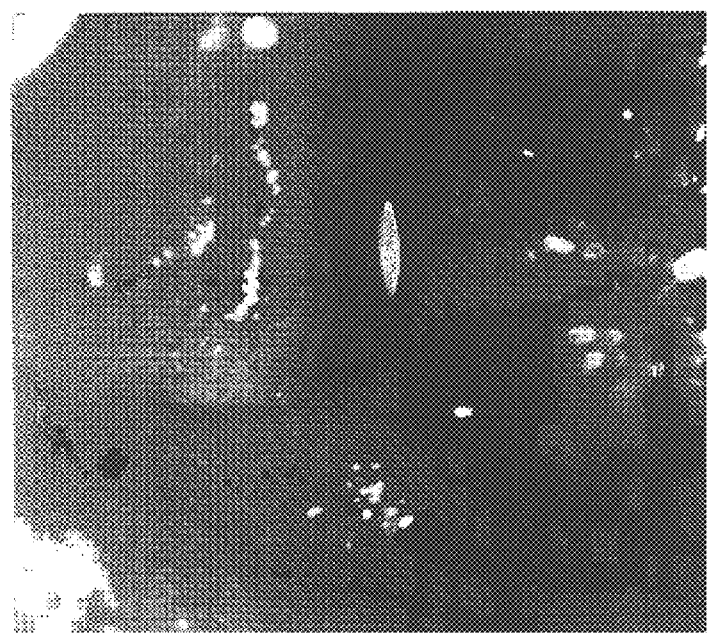

The proper environmental stimuli convert MSCs into cardiac myocytes. Differentiation of mesenchymal stem cells to the cardiac lineage is controlled by factors present in the cardiac environment. Exposure of MSCs to a simulated cardiac environment directs these cells to cardiac differentiation as detected by expression of specific cardiac muscle lineage markers. Local chemical, electrical and mechanical environmental influences alter pluripotent MSCs and convert the cells grafted into the heart into the cardiac lineage.

Early in embryonic development following the epithelia-mesenchyme transition, the presumptive heart mesenchyme from the left and right sides of the body migrate to the ventral midline. Here, interaction with other cell types induces continued cardiogenesis. In vitro conversion of MSCs to cardiomyocytes is tested by co-culture or fusion with murine embryonic stem cells or cardiomyocytes, treatment of MSCs with cardiac cell lysates, incubation with specific soluble growth factors, or exposure of MSCs to mechanical stimuli and electrical stimulation.

A series of specific treatments applicable to MSCs to induce expression of cardiac specific genes are disclosed herein. The conditions are effective on rat, canine and human MSCs. Treatments of MSCs include (1) co-culturinz MSCs with fetal, neonatal and adult rat cardiac cells, (2) use of chemical fusigens (e.g., polyethylene glycol or sendai virus) to create heterokaryons of MSCs with fetal, neonatal and adult cardiomyocytes, (3) incubating MSCs with extracts of mammalian hearts, including the extracellular matrix and related molecules found in heart tissue, (4) treatment of MSCs with growth factors and differentiating agents, (5) mechanical and/or electrical stimulation of MSCs, and (6) mechanically and/or electrically coupling MSCs with cardiomyocytes. MSCs that progress towards cardiomyocytes first express proteins found in fetal cardiac tissue and then proceed to adult forms. Detection of expression of cardiomyocyte specific proteins is achieved using antibodies to, for example, myosin heavy chain monoclonal antibody MF 20 (MF20), sarcoplasmic reticulum calcium ATPase (SERCA1) (mnAb 10D1) or gap junctions using antibodies to connexin 43.

Cardiac injury promotes tissue responses which enhance myogenesis using implanted MSCs. Thus, MSCs are introduced to the infarct zone to reduce the degree of scar formation and to augment ventricular function. New muscle is thereby created within an infarcted myocardial segment. MSCs are directly infiltrated into the zone of infarcted tissue. The integration and subsequent differentiation of these cells is characterized, as described above. Timing of intervention is designed to mimic the clinical setting where patients with acute myocardial infarction would first come to medical attention, receive first-line therapy, followed by stabilization, and then intervention with myocardial replacement therapy if necessary.

Of the four chambers of the heart, the left ventricle is primarily responsible for pumping blood under pressure through the body's circulatory system. It has the thickest myocardial walls and is the most frequent site of myocardial injury resulting from congestive heart failure. The degree of advance or severity of the congestive heart failure ranges from those cases where heart transplantation is indicated as soon as a suitable donor organ becomes available to those where little or no permanent injury is observed and treatment is primarily prophylactic.

The severity of resulting myocardial infarction, i.e. the percentage of muscle mass of the left ventricle that is involved can range from about 5 to about 40 percent. This represents affected tissue areas, whether as one contiguous ischemia or the sum of smaller ischemic lesions, having horizontal affected areas from about 2 $cm^2$ to about 6 $cm^2$ and a thickness of from 1–2 mm to 1–1.5 cm. The severity of the infarction is significantly affected by which vessel(s) is involved and how much time has passed before treatment intervention is begun.

The mesenchymal stem cells used in accordance with the invention are, in order of preference, autologous, allo-eneic or xenogeneic, and the choice can largely depend on the urgency of the need for treatment. A patient presenting an imminently life threatening condition may be maintained on a heart/lung machine while sufficient numbers of autologous MSCs are cultured or initial treatment can be provided using other than autologous MSCs.

The MSC therapy of the invention can be provided by several routes of administration, including the following. First, intracardiac muscle injection, which avoids the need for an open surgical procedure, can be used where the MSCs are in an injectible liquid suspension preparation or where they are in a biocompatible medium which is injectible in liquid form and becomes semi-solid at the site of damaged myocardium. A conventional intracardiac syringe or a controllable arthroscopic delivery device can be used so long as the needle lumen or bore is of sufficient diameter (e.g. 30 gauge or larger) that shear forces will not damage the MSCs. The injectible liquid suspension MSC preparations can also be administered intravenously, either by continuous drip or as a bolus. During, open surgical procedures, involving direct physical access to the heart, all of the described forms of MSC delivery preparations are available options.

As a representative example of a dose range is a volume of about 20 to about 50 $\mu l$ of injectible suspension containing 10–40×$10^6$ MSCs/ml. The concentration of cells per unit volume, whether the carrier medium is liquid or solid remains within substantially the same range. The amount of MSCs delivered will usually be greater when a solid, "patch" type application is made during an open procedure, but follow-up therapy by injection will be as described above. The frequency and duration of therapy will, however, vary depending on the degree (percentage) of tissue involvement, as already described (e.g. 5–40% left ventricular mass).

In cases having in the 5–10% range of tissue involvement, it is possible to treat with as little as a single administration of one million MSCs in 20–50 μl of injection preparation. The injection medium can be any pharmaceutically acceptable isotonic liquid. Examples include phosphate buffered saline (PBS), culture media such as DMEM (preferably serum-free), physiological saline or 5% dextrose in water (D5 W).

In cases having more in a range around the 20% tissue involvement severity level, multiple injections of 20–50 μl ($10-40\times10^6$ MSCs/nil) are envisioned. Follow-up therapy may involve additional dosings.

In very severe cases, e.g. in a range around the 40% tissue involvement severity level, multiple equivalent doses for a more extended duration with long term (up to several months) maintenance dose aftercare may well be indicated.

The present invention is further illustrated, but not limited, by the following example.

EXAMPLE 1

Implantation of MSCs in Normal Cardiac Muscle

In using MSCs, it is desirable to maintain cell-cell contact in vivo for the conversion of MSCs to the muscle lineage. Environmental signals identified above act in concert with mechanical and electrical signaling in vivo to lead to cardiac differentiation.

Primary human MSCs (hMSCs) are introduced into athymic rat myocardial tissue by direct injection. The integration of implanted cells, their subsequent differentiation, formation of junctions with cardiac cells, and their long-term survival are characterized with light microscopy, histology, confocal immunofluorescence microscopy, electron microscopy and in situ hybridization.

Whether human MSCs are appropriately grafted into cardiac muscle of athymic rats (strain HSD:RH-RNU/RNU), which lack the immune responses necessary to destroy many foreign cells, is also examined.

Rat MSCs are grafted into the heart muscles of rats. To analyze the injected cells over several weeks and to minimize the possibility of immune system rejection, MSCs are harvested from Fisher 344 rats, the same inbred strain (identical genotype) as the intended MSC recipients.

The MSCs can be marked in a variety of ways prior to their introduction into the recipient. This makes it possible to trace the fate of the MSCs as they proliferate and differentiate in the weeks following the MSC implant. Several methods are utilized to positively identify the injected cells: membrane lipid dyes PKH26 or CM-DI I and genetic marking with adeno-associated virus (AAV) or retroviruses, such as Maloney murine leukemia virus expressing green fluorescent protein (GFP) or galactosidase. PCR is also used to detect the Y chromosome marker of male cells implanted into female animals. The dye-labeled cells are readily detected and offer the simplest method to directly follow the injected cells. This method is reliable for times out to at least 4 weeks. On the day of introduction to recipient animals, MSCs are trypsinized and labeled with CM-DI I according to the recommendations of the manufacturer (Molecular Probes). Subconfluent monolayer cultures of MSCs are incubated with 5 mM CM-DI I in serum-free medium for 20 minutes, trypsinized, washed twice in excess dye-free medium, and utilized for injection.

Alternatively, MSCs are genetically marked prior to injections, such as by using AAV-GFP vector. This vector lacks a selectable marker but mediates high-level expression of the transduced genes in a variety of post-mitotic and stem cell types. Recombinant AAV-GFP is added to low density monolayers of MSCs in low serum. Following a four hour incubation at 37° C., the supernatant is removed and replaced with fresh media. At 96 hours after transduction, cells are assayed for green fluorescent protein (GFP) activity. Typically 50% of the cells express the transduced gene. Unselected MSCs on a clonal line, isolated by limiting dilution, are utilized for injection. Cells are collected following trypsin treatment, washed and used at high concentrations for injection (10 to 100 million cells per ml).

Figure 1B:

To test whether the hMSCs became cardiomyocytes in the heart environment, the hearts of ten week old athymic rats were injected with dye labeled or GFP-labeled human MSCs. All procedures were performed under strict sterile conditions. The animals were placed in a glass jar containing a methoxyflurane anesthesia soaked sponge. Under sterile conditions, a 20 mm anterior thoracotomy was performed, and following visualization of the left ventricle, 10 μl of the cell suspension, containing 10,000 to 100,000 MSCs in serum-free medium were injected into the left ventricular apex using a 30 gauge needle. The procedure was performed rapidly with endotracheal intubation and mechanical ventilation assist. The incision was closed with sutures. Ventilation assist was normally unnecessary after a short period following chest closure. FIG. 1A shows the low magnification image of a rat heart which was injected with dye labeled cells and later, a T-incision had been made at the site to reveal the injected cells in the ventrical wall. FIG. 1A is a gross photo of the incised heart. FIGS. 1B and 1C reveal the labeled MSCs in the ventricle wall. FIG. 1C shows that the cells were present in the outer 1–2 mm of the 3 mm thick rat cardiac muscle.

When sacrificed, the heart is removed, examined by light microscopy for the presence of vascular thrombi or emboli, paraffin-embedded, and sectioned. The histology of serial sections is examined to determine the fate of dye-stained cells. Sections are then tested for imrnmunohistochemical markers of cardiac muscle in the areas of the introduced MSCs to ascertain whether donor MSCs have differentiated into cardiomyocytes in vivo. Implantation surgeries are carried out on animals to be sacrificed at 1, 2, 4, and 6 weeks (4 animals at each time point) and the hearts which received implants are analyzed histologically and immunologically.

For phenotypic characterization, the hearts are removed and processed for histology by immunofluorescence microscopy. Differentiation of MSCs is determined by the immunofluorescence localization of sacomeric myosin heavy chain, SERCA1 and phospholamban. The sequence-specific antibody to gap junction protein connexin 43, which is commercially available (Zymed) and detects gap junctions in cardiac tissue is used.

MSCs are also implanted in biomatrix materials to determine if enhanced grafting would be observed, such as type I collagen. The MSCs are rapidly mixed with the matrix in a small volume and injected into the ventricle wall. The biomatrices are used at concentrations of 0.1 mg/rni or greater. For example, the biomatrices may be used at concentrations of 1 to 3 mg/ml containing 10 to 100 million cells/mnl. The tissue is analyzed at times of 1, 2, 4, and 6 weeks as described above.

EXAMPLE 2

Regeneration of Heart Valves Using MSCs

Xenograft or homograft valves are made acellular by freeze-drying, which leads to cellular death, or by enzymatic treatment followed by detergent extraction of cells and cell debris. This latter approach was taken by Vesely and coworkers with porcine valves to be repopulated with dermal or aortic fibroblasts. Curtil et al. 1997 used a freeze-dried porcine valve and attempted repopulation of the valve with human fibroblasts and endothelial cells. These studies were preliminary and limited to short term studies in vitro.

The acellular valve to be populated by autologous hMSCs is incubated with culture expanded hMSCs in a tumbling vessel to ensure loading of cells to all valve surfaces. The valve is then cultured with the hMSCs for 1–2 weeks to allow the hMSCs to infiltrate and repopulate the valve. Within the culture vessel, the valve is then attached to a pump to allow the actuation of the valve leaflets and simulate the pumping motion present in the body. The valve is maintained in the pumping mode for 1–2 weeks to allow cellular remodeling associated with the stresses of the pumping action. Once sufficient cellular remodeling has occurred, the valve is implanted into the body of the patient.

Another embodiment of this aspect of the invention is to first repopulate the valve with hMSCs and to later incubate the valve tissue during the pumping stage with autologous smooth muscle cells isolated from a vascular graft which will line the lumen of the valve.

What is claimed is:

1. A process for producing cardiac muscle cells in the heart of an individual in need thereof, comprising:

administering to said individual autologoue or allogenic mesenchymal stem cells in an amount effective to produce cardiac muscle cells in the heart of said individual, said administered mesenchymal stem cells differentiating into cardiac muscle cells thereby producing cardiac muscle cells in the heart of said individual.

2. The process of claim 1 wherein said mesenchymal stem cells are administered to an individual to regenerate or repair cardiac muscle that has been damaged through disease.

3. The process of claim 2 wherein said mesenchymal stem cells are administered to an individual who has suffered myocardial infarction.

4. The process of claim 2 wherein said mesenchymal stem cells are administered directly to the heart.

5. The process of claim 2 wherein said mesenchymal stem cells are administered systemically.

6. The process of claim 5 wherein said mesenchymal stem cells are administered by injection.

7. The process of claim 2 wherein said mesenchymal stem cells are human.

8. The process of claim 7 wherein said mesenchymal stem cells are administered to an individual who has suffered myocardial infarction.

9. The process of claim 8 wherein said mesenchymal stem cells are administered directly to the heart.

10. The process of claim 8 wherein said the mesenchymal stem cells are administered systemically.

11. A process for reducing scar formation in infarcted heart tissue, comprising:

administering to an individual having infarcted heart tissue autologous or allogenic mesenchymal stem cells in an amount effective to produce cardiac muscle cells in the heart of said individual, said administered mesenchymal stem cells differentiating into cardiac muscle cells, and wherein said cardiac muscle cells produce cardiac muscle, thereby reducing scar formation in said infarcted heart tissue.

12. The process of claim 11 wherein said the mesenchymal stem cells are administered systemically.

13. The process of claim 12 wherein said mensechymal stem cells are administered by injection.

14. The process of claim 11 wherein said mesenchymal stem cells are human.

15. The process of claim 14 wherein said mesenchymal stem cells are administered directly to the heart.

16. The process of claim 14 wherein said mesenchymal stem cells are administered systemically.

17. The process of claim 16 wherein said mensechymal stem cells are administered by injection.

* * * * *